US007986993B1

(12) United States Patent
Levine

(10) Patent No.: US 7,986,993 B1
(45) Date of Patent: *Jul. 26, 2011

(54) IMPLANTABLE CARDIAC DEVICE PROVIDING AV INTERVAL HYSTERESIS TO PROMOTE INTRINSIC CONDUCTION WHILE PROVIDING PMT AVOIDANCE AND METHOD

(75) Inventor: Paul A. Levine, Santa Clarita, CA (US)

(73) Assignee: Pacesetter, Inc., Sylmar, CA (US)

( * ) Notice: Subject to any disclaimer, the term of this patent is extended or adjusted under 35 U.S.C. 154(b) by 1004 days.

This patent is subject to a terminal disclaimer.

(21) Appl. No.: 11/769,602

(22) Filed: Jun. 27, 2007

(51) Int. Cl.
*A61N 1/18* (2006.01)

(52) U.S. Cl. .............................................. 607/9; 607/17

(58) Field of Classification Search .................. None
See application file for complete search history.

(56) References Cited

U.S. PATENT DOCUMENTS

| 4,788,980 | A | 12/1988 | Mann et al. |
| 5,674,257 | A | 10/1997 | Stroebel |
| 5,861,007 | A | 1/1999 | Hess et al. |
| 6,243,606 | B1 | 6/2001 | Mann et al. |
| 6,259,950 | B1 | 7/2001 | Mann et al. |
| 6,263,244 | B1 | 7/2001 | Mann et al. |
| 6,285,908 | B1 | 9/2001 | Mann et al. |
| 6,498,949 | B2 | 12/2002 | Levine et al. |
| 6,584,354 | B1 | 6/2003 | Mann et al. |
| 6,618,622 | B1 | 9/2003 | Mann et al. |
| 6,792,307 | B1* | 9/2004 | Levine et al. .................. 607/9 |
| 6,862,477 | B1 | 3/2005 | Mo |
| 7,146,215 | B1 | 12/2006 | Mo |
| 7,424,323 | B1 | 9/2008 | Reiss et al. |
| 2008/0091244 | A1* | 4/2008 | Richardson ....................... 607/9 |
| 2008/0140147 | A1* | 6/2008 | Husby ............................. 607/30 |
| 2009/0005828 | A1* | 1/2009 | Levine ............................ 607/14 |

FOREIGN PATENT DOCUMENTS

| EP | 0308535 B1 | 3/1993 |
| WO | 2006065707 A2 | 6/2006 |

OTHER PUBLICATIONS

Olshansky, Brian MD et al., "Pacemaker-Mediated Tachycardia," www.emedicine.com, Aug. 9, 2006.
Levine, Paul A. MD, "Postventricular Atrial Refractory Periods and Pacemaker Mediated Tachycardias," Clin. Prog. in Pacing and Electrophysiol. 1983:1(4):394-401.
Dennis, Malcolm J. et al., "Pacemaker Mediated Tachycardia as a Complication of the Autointrinsic Conduction Search Function," PACE. 2004;27(Pt I):824-826.
Levine, Paul A., "Letters to the Editor," PACE. 2004;27:1691-1693.
NonFinal Office Action, mailed Oct. 9, 2007—Related U.S. Appl. No. 11/218,770.
Notice of Allowance, mailed Mar. 20, 2008—Related U.S. Appl. No. 11/218,770.

* cited by examiner

*Primary Examiner* — Carl H. Layno
*Assistant Examiner* — Jon-Eric C. Morales

(57) ABSTRACT

An implantable cardiac stimulation device provides AV interval hysteresis to promote intrinsic conduction while providing PMT avoidance. The device comprises a pulse generator that provides atrial and ventricular pacing stimulation pulses on demand separated by an AV interval, an AV hysteresis circuit that extends the AV interval from a base AV interval to an extended AV interval to promote intrinsic heart activity, and a refractory circuit that establishes a PVARP following each provided ventricular pacing pulse including a lengthened PVARP longer in duration than a normal PVARP responsive to the AV hysteresis circuit extending the AV interval from the base AV interval to the extended AV interval.

17 Claims, 4 Drawing Sheets

IMPLANTABLE CARDIAC DEVICE PROVIDING AV INTERVAL HYSTERESIS TO PROMOTE INTRINSIC CONDUCTION WHILE PROVIDING PMT AVOIDANCE AND METHOD

CROSS-REFERENCE TO RELATED APPLICATIONS

This application is related to copending U.S. patent application Ser. No. 11/218,770, filed Sep. 1, 2005, titled "Implantable Cardiac Stimulation Device Providing Autocapture with PMT Avoidance and Method."

FIELD OF THE INVENTION

The present invention generally relates to an implantable cardiac device. The present invention more particularly relates to an implantable pacemaker which provides AV interval hysteresis to encourage intrinsic conduction of a patient's heart while avoiding pacemaker mediated tachycardia (PMT).

BACKGROUND OF THE INVENTION

Implantable cardiac devices are well known in the art. They may take the form of implantable defibrillators or cardioverters which treat accelerated rhythms of the heart such as fibrillation. They may also take the form of implantable pacemakers which maintain the heart rate above a prescribed limit, such as, for example, to treat a bradycardia. Implantable cardiac devices are also known which incorporate both a pacemaker and a defibrillator.

A pacemaker is comprised of two major components. One component is a pulse generator which generates the pacing stimulation pulses and includes the electronic circuitry and the power cell or battery. The other component is the lead, or leads, which electrically couple the pacemaker to the heart.

Pacemakers deliver pacing pulses to the heart to cause the stimulated heart chamber to contract when the patient's own intrinsic rhythm fails. To this end, pacemakers include sensing circuits that sense cardiac activity for the detection of intrinsic cardiac events such as intrinsic atrial events (P waves) and intrinsic ventricular events (R waves). By monitoring such P waves and/or R waves, the pacemaker circuits are able to determine the intrinsic rhythm of the heart and provide stimulation pacing pulses that force atrial and/or ventricular depolarizations at appropriate times in the cardiac cycle when required to help stabilize the electrical rhythm of the heart.

Pacemakers are described as single-chamber or dual-chamber systems. A single-chamber system stimulates and senses the same chamber of the heart (atrium or ventricle). A dual-chamber system stimulates and/or senses in both chambers of the heart (atrium and ventricle). Dual-chamber systems may typically be programmed to operate in either a dual-chamber mode or a single-chamber mode. Further, pacing systems are known which pace in multiple sites. For example, biventricular pacing paces in both ventricles and biatrial pacing paces in both atria. Hence, it is possible, that a heart may be paced in all four of its chambers.

A popular mode of operation for dual-chamber pacemakers is the DDD mode. Specifically, DDD systems provide atrial pacing during atrial bradycardia, ventricle pacing during ventricular bradycardia, and atrial and ventricular pacing during combined atrial and ventricular bradycardia or heart block also known as AV block. In addition, DDDR systems monitor patient activity levels for controlling pacing rate to more closely approximate the normal response of the heart to exercise, or other physiological activity demanding a faster heart rate.

Recent studies have indicated that ventricular pacing in the setting of intact AV nodal conduction has an adverse impact compared to permitting intrinsic ventricular contractions. Hence, pacing therapies have been advanced which encourage intrinsic ventricular activity.

One such system employs an auto intrinsic conduction search (AICS) wherein the pacemaker utilizes two AV intervals. The first AV interval is a programmable base AV interval to support ventricular demand pacing. It may be, for example, on the order of two hundred (200) milliseconds. The second AV interval is an extended AV interval which may be thought of as comprising the base AV interval with an AV interval extension added to its end. The AV interval extension may be on the order of one hundred (100) milliseconds, for example. Hence, in this example, the extended AV interval would total three hundred (300) milliseconds.

The AICS may be implemented as follows. The device paces in a demand mode with the base AV interval. After a timed interval of five minutes, for example, the device extends the AV interval to the extended AV interval for one cycle to encourage intrinsic ventricular activity. The device does not reset to the shorter base AV interval until a ventricular pacing pulse is administered.

Other methods to promote or encourage intrinsic conduction through AV interval extension have been advanced. Hence, the term AV hysteresis is meant to encompass all such methods involving AV interval extension to encourage intrinsic heart activity.

Unfortunately, some problems can arise as a result of an AV interval extension during the implementation of AV hysteresis. During the extended AV interval, the atrium may have recovered on a physiologic basis to allow retrograde conduction to occur and the initiation of a pacemaker mediated tachycardia (PMT). Repeated stimulation at a high rate can there after be sustained by heart tissue retrograde conduction and by pacemaker anterograde conduction.

Methods for preventing PMT are well known in the art. One such known method involves the use of programmable post-ventricular atrial refractory periods (PVARP), where the PVARP is programmed to be longer than the retrograde conduction interval. Unfortunately, standard PVARP intervals in the setting of AV interval extension during AV hysteresis have not always been successful in avoiding the generation of a PMT. Hence, there remains room for improving AV hysteresis and preventing PMT's during their use.

In addition to potential PMT's, other arrhythmic heart rhythms may result from AV hysteresis. One such arrhythmic heart rhythm is a repetitive non-reentrant ventriculo-atrial synchronous (RNRVAS) rhythm. The RNRVAS rhythm is fully described, for example, in U.S. Pat. No. 6,498,949 B2, which patent is incorporated herein in its entirety.

Another arrhythmic heart rhythm that may result from AV hysteresis is AV nodal reentrant tachycardia (AVNRT). In this case, a P wave coinciding with an extended PVARP is not tracked, however, if it is conducted with a long PR interval, it may return in a retrograde manner through a second pathway within the AV node or peri-AV nodal tissues allowing for sustained intrinsic supraventricular reentrant tachycardia.

It would be most desirable if an implantable cardiac stimulation device could both avoid PMT's and deal with other arrhythmic cardiac rhythms during or as a result of AV hysteresis. The present invention addresses this and other issues.

SUMMARY OF THE INVENTION

The invention, in one embodiment, provides an implantable cardiac stimulation system comprising a pulse generator that provides atrial and ventricular pacing stimulation pulses on demand separated by an AV interval, an AV hysteresis circuit that extends the AV interval from a base AV interval to an extended AV interval to promote intrinsic heart activity, and a refractory circuit that establishes a PVARP following each provided ventricular pacing pulse including a lengthened PVARP longer in duration than a normal PVARP responsive to the AV hysteresis circuit extending the AV interval from the base AV interval to the extended AV interval.

The refractory circuit may establish the lengthened PVARP by providing a PVARP extension to a base PVARP. The PVARP extension may be of fixed duration. The PVARP extension may be a programmable parameter.

The device may further comprise a sensing circuit that senses retrograde P waves occurring during an extended PVARP. The AV hysteresis circuit may restore the AV interval to the base AV interval in response to the sensing circuit sensing a retrograde P wave during an extended PVARP. The AV refractory circuit may restore the PVARP to the normal PVARP in response to the sensing circuit sensing a retrograde P wave during an extended PVARP. The device may further comprise an arrhythmia detector that detects for an arrhythmic cardiac rhythm responsive to the sensing circuit sensing a retrograde P wave occurring during an extended PVARP. The device may further comprise a therapy control that provides a corrective therapy responsive to the arrhythmia detector detecting an arrhythmic cardiac rhythm.

The AV hysteresis circuit may restore the AV interval to the Base AV interval and the refractory circuit may restore the PVARP to a base PVARP responsive the therapy circuit providing the corrective therapy. The arrhythmic cardiac rhythm may be a repetitive non-reentrant ventriculo-atrial synchronous (RNRVAS) rhythm. The pulse generator may further provide an atrial escape interval and the therapy control may lengthen the atrial escape interval responsive to the arrhythmia detector detecting an RNRVAS rhythm.

In another embodiment, an implantable cardiac stimulation system comprises a pulse generator that provides atrial and ventricular pacing stimulation pulses on demand. The pulse generator further provides an AV interval. The device further comprises an AV hysteresis circuit that extends the AV interval from a base AV interval to an extended AV interval to promote intrinsic heart activity, a refractory circuit that establishes a PVARP following each provided ventricular pacing pulse including a lengthened PVARP longer in duration than a normal PVARP responsive to the AV hysteresis circuit extending the AV interval from the base AV interval to the extended AV interval, and a sensing circuit that senses retrograde P waves occurring during an extended PVARP. The AV hysteresis circuit restores the AV interval to the base AV interval in response to the sensing circuit sensing a retrograde P wave during an extended PVARP.

In another embodiment, a method for use in an implantable cardiac stimulation system comprises providing atrial and ventricular pacing stimulation pulses on demand with an AV interval, extending the AV interval from a base AV interval to an extended AV interval to promote intrinsic heart activity, establishing a PVARP following each provided ventricular pacing pulse, and lengthening the PVARP to a PVARP longer in duration than a normal PVARP responsive to extending the AV interval from the base AV interval to the extended AV interval.

BRIEF DESCRIPTION OF THE DRAWINGS

Further features and advantages of the present invention may be more readily understood by reference to the following description taken in conjunction with the accompanying drawings, in which.

DESCRIPTION OF THE PREFERRED EMBODIMENTS

The following description is of the best mode presently contemplated for practicing the invention. This description is not to be taken in a limiting sense but is made merely for the purpose of describing the general principles of the invention. The scope of the invention should be ascertained with reference to the issued claims. In the description of the invention that follows, like numerals or reference designators will be used to refer to like parts or elements throughout.

Figure 1:
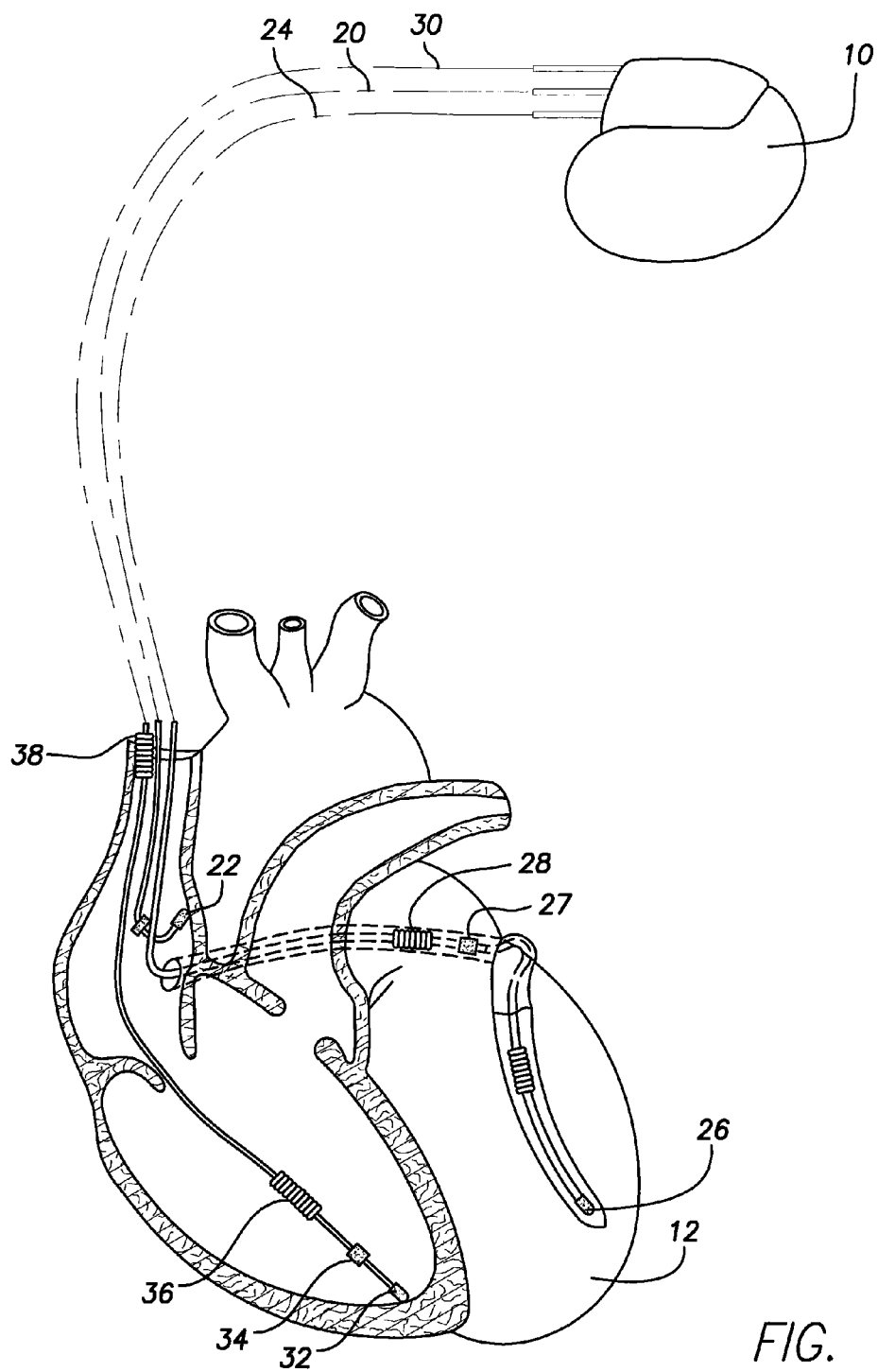
FIG. 1 is a simplified diagram illustrating an implantable stimulation device in electrical communication with at least three leads implanted into a patient's heart for delivering multi-chamber stimulation and shock therapy.

As shown in FIG. 1, there is a stimulation device 10 in electrical communication with a patient's heart 12 by way of three leads, 20, 24 and 30, suitable for delivering multi-chamber stimulation and shock therapy. To sense atrial cardiac signals and to provide right atrial chamber stimulation therapy, the stimulation device 10 is coupled to an implantable right atrial lead 20 having at least an atrial tip electrode 22, which typically is implanted in the patient's right atrial.

To sense left atrial and ventricular cardiac signals and to provide left chamber pacing therapy, the stimulation device 10 is coupled to a "coronary sinus" lead 24 designed for placement in the "coronary sinus region" via the coronary sinus ostium for positioning a distal electrode adjacent to the left ventricle and/or additional electrode(s) adjacent to the left atrium. As used herein, the phrase "coronary sinus region" refers to the venous vasculature of the left ventricle, including any portion of the coronary sinus, great cardiac vein, left marginal vein, left posterior ventricular vein, middle cardiac vein, and/or small cardiac vein or any other cardiac vein accessible by the coronary sinus. Accordingly, an exemplary coronary sinus lead 24 is designed to receive left atrial and ventricular cardiac signals and to deliver left ventricular pacing therapy using at least a left ventricular tip electrode 26, left atrial pacing therapy using at least a left atrial ring electrode 27, and shocking therapy using at least a left atrial coil electrode 28.

The stimulation device 10 is also shown in electrical communication with the patient's heart 12 by way of an implantable right ventricular lead 30 having, in this embodiment, a right ventricular tip electrode 32, a right ventricular ring electrode 34, a right ventricular (RV) coil electrode 36, and an SVC coil electrode 38. Typically, the right ventricular lead 30 is transvenously inserted into the heart 12 so as to place the right ventricular tip electrode 32 in the right ventricle so that the RV coil electrode will be positioned in the right ventricle and the SVC coil electrode 38 will be positioned in the superior vena cava. Accordingly, the right ventricular lead 30 is capable of receiving cardiac signals, and delivering stimulation in the form of pacing and shock therapy to the right ventricle.

Figure 2:
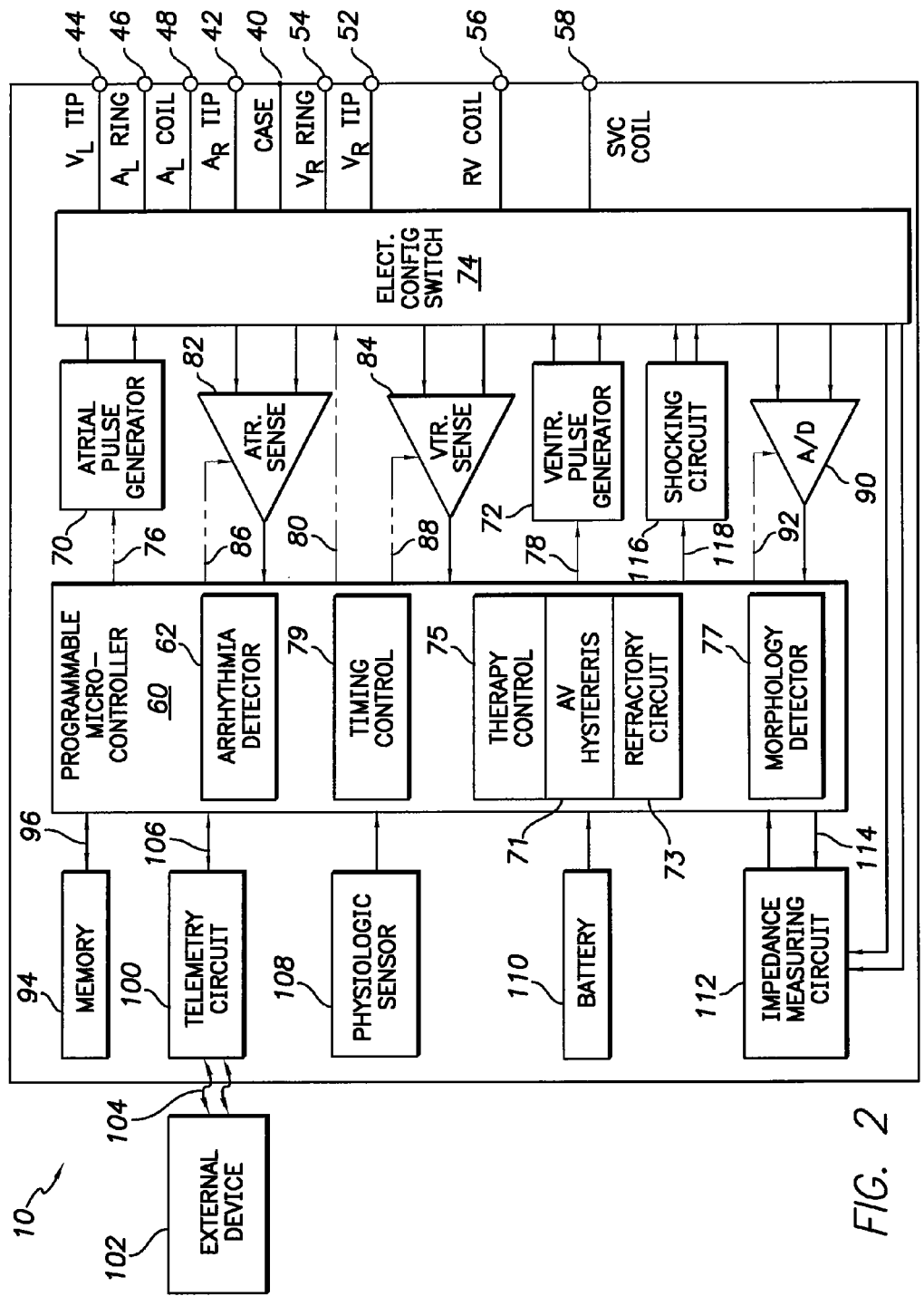
FIG. 2 is a functional block diagram of the implantable stimulation device of FIG. 1 illustrating an embodiment of the present invention.

As illustrated in FIG. 2, a simplified block diagram is shown of the multi-chamber implantable stimulation device 10, which is capable of treating both fast and slow arrhythmias with stimulation therapy, including cardioversion, defibrillation, and pacing stimulation. While a particular multi-chamber device is shown, this is for illustration purposes only, and one of skill in the art could readily duplicate, eliminate or disable the appropriate circuitry in any desired combination to provide a device capable of treating the appropriate chamber(s) with cardioversion, defibrillation and pacing stimulation.

The housing 40 for the stimulation device 10, shown schematically in FIG. 2, is often referred to as the "can", "case" or "case electrode" and may be programmably selected to act as the return electrode for all "unipolar" modes. The housing 40 may further be used as a return electrode alone or in combination with one or more of the coil electrodes, 28, 36 and 38, for shocking purposes. The housing 40 further includes a connector (not shown) having a plurality of terminals, 42, 44, 46, 48, 52, 54, 56, and 58 (shown schematically and, for convenience, the names of the electrodes to which they are connected are shown next to the terminals). As such, to achieve right atrial sensing and pacing, the connector includes at least a right atrial tip terminal ($A_R$ TIP) 42 adapted for connection to the atrial tip electrode 22.

To achieve left chamber sensing, pacing and shocking, the connector includes at least a left ventricular tip terminal ($V_L$ TIP) 44, a left atrial ring terminal ($A_L$ RING) 46, and a left atrial shocking terminal ($A_L$ COIL) 48, which are adapted for connection to the left ventricular ring electrode 26, the left atrial tip electrode 27, and the left atrial coil electrode 28, respectively.

To support right chamber sensing, pacing and shocking, the connector further includes a right ventricular tip terminal ($V_R$ TIP) 52, a right ventricular ring terminal ($V_R$ RING) 54, a right ventricular shocking terminal ($R_V$ COIL) 56, and an SVC shocking terminal (SVC COIL) 58, which are adapted for connection to the right ventricular tip electrode 32, right ventricular ring electrode 34, the RV coil electrode 36, and the SVC coil electrode 38, respectively.

At the core of the stimulation device 10 is a programmable microcontroller or processor 60 which controls the various modes of stimulation therapy. As is well known in the art, the microcontroller 60 typically includes a microprocessor, or equivalent control circuitry, designed specifically for controlling the delivery of stimulation therapy and may further include RAM or ROM memory, logic and timing circuitry, state machine circuitry, and I/O circuitry. Typically, the microcontroller 60 includes the ability to process or monitor input signals (data) as controlled by a program code stored in a designated block of memory. The details of the design and operation of the microcontroller 60 are not critical to the present invention. Rather, any suitable microcontroller 60 may be used that carries out the functions described herein. The use of microprocessor-based control circuits for performing timing and data analysis functions are well known in the art.

As shown in FIG. 2, an atrial pulse generator 70 and a ventricular pulse generator 72 generate pacing stimulation pulses for delivery by the right atrial lead 20, the right ventricular lead 30, and/or the coronary sinus lead 24 via an electrode configuration switch 74. It is understood that in order to provide stimulation therapy in each of the four chambers of the heart, the atrial and ventricular pulse generators, 70 and 72, may include dedicated, independent pulse generators, multiplexed pulse generators, or shared pulse generators. The pulse generators, 70 and 72, are controlled by the microcontroller 60 via appropriate control signals, 76 and 78, respectively, to trigger or inhibit the stimulation pulses.

The microcontroller 60 further includes timing control circuitry 79 which is used to control the timing of such stimulation pulses (e.g., pacing rate, atrio-ventricular (AV) interval or delay, ventricular-atrio (VA) interval or delay, atrial interconduction (A-A) delay, or ventricular interconduction (V-V) delay, etc.) as well as to keep track of the timing of blanking intervals, noise detection windows, evoked response windows, alert intervals, marker channel timing, etc., which is well known in the art. The microcontroller 60 also includes a refractory circuit 73. The refractory circuit 73 times refractory periods, including post ventricular atrial refractory periods (PVARP) as described subsequently.

The switch 74 includes a plurality of switches for connecting the desired electrodes to the appropriate I/O circuits, thereby providing complete electrode programmability. Accordingly, the switch 74, in response to a control signal 80 from the microcontroller 60, determines the polarity of the stimulation pulses (e.g., unipolar, bipolar, combipolar, etc.) by selectively closing the appropriate combination of switches (not shown) as is known in the art.

Atrial sensing circuits 82 and ventricular sensing circuits 84 may also be selectively coupled to the right atrial lead 20, coronary sinus lead 24, and the right ventricular lead 30, through the switch 74 for detecting the presence of cardiac activity in each of the four chambers of the heart. Accordingly, the atrial (ATR. SENSE) and ventricular (VTR. SENSE) sensing circuits, 82 and 84, may include dedicated sense amplifiers, multiplexed amplifiers, or shared amplifiers. The switch 74 determines the "sensing polarity" of the cardiac signal by selectively closing the appropriate switches, as is also known in the art. In this way, the clinician may program the sensing polarity independent of the stimulation polarity.

Each sensing circuit, 82 and 84, preferably employs one or more low power, precision amplifiers with programmable gain and/or automatic gain control, bandpass filtering, and a threshold detection circuit, as known in the art, to selectively sense the cardiac signal of interest. The automatic gain control enables the device 10 to deal effectively with the difficult problem of sensing the low amplitude signal characteristics of atrial or ventricular fibrillation. The outputs of the atrial and ventricular sensing circuits, 82 and 84, are connected to the microcontroller 60 which, in turn, are able to trigger or inhibit the atrial and ventricular pulse generators, 70 and 72, respectively, in a demand fashion in response to the absence or presence of cardiac activity in the appropriate chambers of the heart.

An arrhythmia detector 62 utilizes the atrial and ventricular sensing circuits, 82 and 84, to sense cardiac signals to determine whether a rhythm is physiologic or pathologic. As used herein "sensing" is reserved for the noting of an electrical signal, and "detection" is the processing of these sensed signals and noting the presence of an arrhythmia. The timing intervals between sensed events (e.g., P-waves, R-waves, and depolarization signals associated with fibrillation which are sometimes referred to as "F-waves" or "Fib-waves") are then classified by the microcontroller 60 by comparing them to a predefined rate zone limit (i.e., bradycardia, normal, low rate VT, high rate VT, and fibrillation rate zones) and various other characteristics (e.g., sudden onset, stability, physiologic sensors, and morphology, etc.) in order to determine the type of remedial therapy that is needed (e.g., bradycardia pacing, anti-tachycardia pacing, cardioversion shocks or defibrillation shocks, collectively referred to as "tiered therapy").

Cardiac signals are also applied to the inputs of an analog-to-digital (A/D) data acquisition system 90. The data acquisition system 90 is configured to acquire intracardiac electrogram signals, convert the raw analog data into a digital signal, and store the digital signals for later processing and/or telemetric transmission to an external device 102. The data acquisition system 90 is coupled to the right atrial lead 20, the coronary sinus lead 24, and the right ventricular lead 30 through the switch 74 to sample cardiac signals across any pair of desired electrodes.

Advantageously, the data acquisition system 90 may be coupled to the microcontroller, or other detection circuitry for detecting an evoked response from the heart 12 in response to an applied stimulus, thereby aiding in the detection of "capture". Capture occurs when an electrical stimulus applied to the heart is of sufficient energy to depolarize the cardiac tissue. The microcontroller 60 detects a depolarization signal during a window following a stimulation pulse, the presence of which indicates that capture has occurred. The microcontroller 60 enables capture detection by triggering the ventricular pulse generator 72 to generate a stimulation pulse, starting a capture detection window using the timing control circuitry 79 within the microcontroller 60, and enabling the data acquisition system 90 via control signal 92 to sample the cardiac signal that falls in the capture detection window and, based on the amplitude, determines if capture has occurred.

Capture detection preferably occurs on a beat-by-beat basis associated with the autocapture algorithm. Preferably, the capture threshold search is performed as previously described.

The microcontroller 60 is further coupled to a memory 94 by a suitable data/address bus 96, wherein the programmable operating parameters used by the microcontroller 60 are stored and modified, as required, in order to customize the operation of the stimulation device 10 to suit the needs of a particular patient. Such operating parameters define, for example, pacing pulse amplitude, pulse duration, electrode polarity, rate, sensitivity, automatic features, arrhythmia detection criteria, and the amplitude, waveshape and vector of each shocking pulse to be delivered to the patient's heart 12 within each respective tier of therapy.

Advantageously, the operating parameters of the implantable device 10 may be non-invasively programmed into the memory 94 through a telemetry circuit 100 in telemetric communication with the external device 102, such as a programmer, transtelephonic transceiver, or a diagnostic system analyzer. The telemetry circuit 100 is activated by the microcontroller by a control signal 106. The telemetry circuit 100 advantageously allows intracardiac electrograms and status information relating to the operation of the device 10 (as contained in the microcontroller 60 or memory 94) to be sent to the external device 102 through an established communication link 104.

In the preferred embodiment, the stimulation device 10 further includes a physiologic sensor 108, commonly referred to as a "rate-responsive" sensor because it is typically used to adjust pacing stimulation rate according to the exercise state of the patient. However, the physiological sensor 108 may further be used to detect changes in cardiac output, changes in the physiological condition of the heart, or diurnal changes in activity (e.g., detecting sleep and wake states). Accordingly, the microcontroller 60 responds by adjusting the various pacing parameters (such as rate, AV Delay, V-V Delay, etc.) at which the atrial and ventricular pulse generators, 70 and 72, generate stimulation pulses.

The stimulation device additionally includes a battery 110 which provides operating power to all of the circuits shown in FIG. 2. For the stimulation device 10, which employs shocking therapy, the battery 110 must be capable of operating at low current drains for long periods of time, and then be capable of providing high-current pulses (for capacitor charging) when the patient requires a shock pulse. The battery 110 must also have a predictable discharge characteristic so that elective replacement time can be detected. Accordingly, the device 10 may employ a power source comprised or one or more lithium salts, for example lithium/silver vanadium pentoxide, or other battery technologies known in the art.

As further shown in FIG. 2, the device 10 is shown as having an impedance measuring circuit 112 which is enabled by the microcontroller 60 via a control signal 114. The known uses for an impedance measuring circuit 120 include, but are not limited to, lead impedance surveillance during the acute and chronic phases for proper lead positioning or dislodgement; detecting operable electrodes and automatically switching to an operable pair if dislodgement occurs; measuring respiration or minute ventilation; measuring thoracic impedance for determining shock thresholds; detecting when the device has been implanted; measuring stroke volume; and detecting the opening of heart valves, etc. The impedance measuring circuit 120 is advantageously coupled to the switch 74 so that any desired electrode may be used. The impedance measuring circuit 112 is not critical to the present invention and is shown for only completeness.

In the case where the stimulation device 10 is intended to operate as an implantable cardioverter/defibrillator (ICD) device, it must detect the occurrence of an arrhythmia, and automatically apply an appropriate electrical shock therapy to the heart aimed at terminating the detected arrhythmia. To this end, the microcontroller 60 further controls a shocking circuit 116 by way of a control signal 118. The shocking circuit 116 generates shocking pulses of low (up to 5 joules), moderate (6-15 joules), or high energy (16 to 40 joules), as controlled by the microcontroller 60. Such shocking pulses are applied to the patient's heart 12 through at least two shocking electrodes, and as shown in this embodiment, selected from the left atrial coil electrode 28, the RV coil electrode 36, and/or the SVC coil electrode 38. As noted above, the housing 40 may act as an active electrode in combination with the RV electrode 36, or as part of a split electrical vector using the SVC coil electrode 38 or the left atrial coil electrode 28 (i.e., using the RV electrode as a common electrode).

Cardioversion shocks are generally considered to be of low to moderate energy level and/or synchronized with an R-wave and/or pertaining to the treatment of tachycardia. Defibrillation shocks are generally of moderate to high energy level, i.e., corresponding to thresholds in the range of 16-40 joules. Although external ICDs deliver the shock asynchronously (since R-waves may be too disorganized and small) in the setting of ventricular fibrillation, the implantable devices still synchronize with a ventricular depolarization signal.

Accordingly, the microcontroller 60 is capable of controlling the delivery of the shocking pulses of various energy levels depending on the detected rate and identification of the rhythm by the implanted ICD.

As may be noted, the device 10 further includes an AV hysteresis circuit 71 and a refractory circuit 73. The AV hysteresis circuit 71 initiates an AV interval extension to encourage intrinsic activity of the heart during demand pacing. The AV hysteresis circuit may be of the type as previously described that extends the AV interval from a base AV interval to an extended AV interval by adding to the base AV interval an AV interval extension. The AV interval extension may be a fixed programmable interval. The AV interval is extended after the time-out of a predetermined time period following the restoration of the AV interval from a previous AV interval extension. The AV interval extension remains until the delivery of a first ventricular pacing pulse is required. When the pacing pulse is issued, the AV interval is restored back to the base value.

According to the broader aspects of the invention, when the AV interval is extended by the AV hysteresis circuit 71, the refractory circuit 73 in turn extends the PVARP from a base value to an extended PVARP by adding a PVARP extension to the base PVARP. The PVARP extended may also be a fixed programmable interval. The extended PVARP is maintained until the AV interval is restored to the base AV interval value. During the PVARP, atrial activity is preferably still sensed but not responded to for initiating a new AV interval. Rather, if a retrograde P wave is sensed by sense amplifier 82 during an extended PVARP, the AV interval is restored to the base AV interval by the AV hysteresis circuit 71 and the PVARP is also restored to its base value by the refractory circuit 73.

The device further includes a therapy control 75 that may be employed to initiate therapy for arrhythmic rhythms sensed after a P wave is sensed during an extended PVARP. The arrhythmic rhythm may be, for example, an RNRVAS rhythm. In this case, the therapy applied may include lengthening the atrial escape interval for at least one cardiac cycle to break the rhythm. The AV interval and the PVARP may then be restored to their base values. As another example, the arrhythmic rhythm may be AVNRT, in which case the extended PVARP may be shortened, thereby allowing the retrograde P wave to be detected to thus trigger a ventricular pulse at a shorter PV delay to preclude further reentry.

Figure 3:
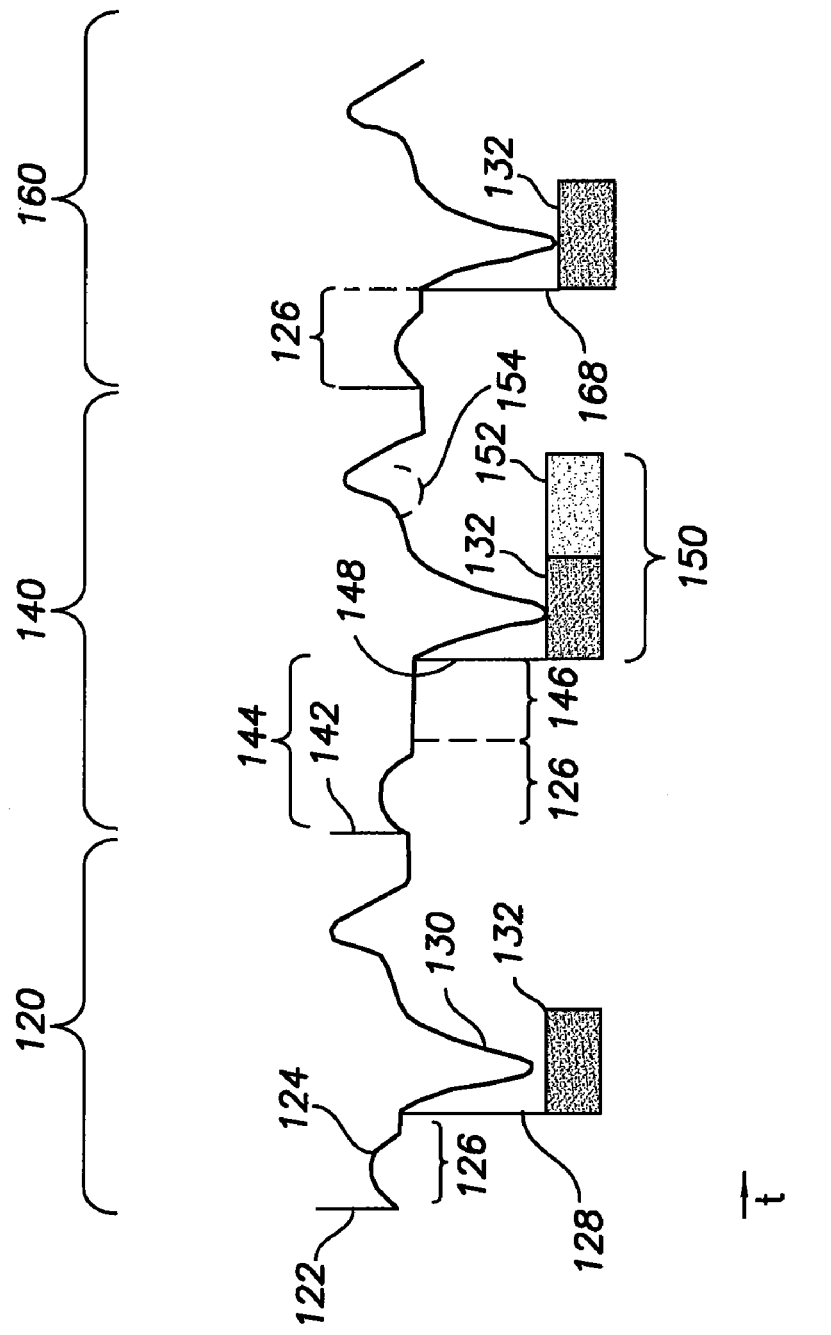
FIG. 3 is a timing diagram illustrating an embodiment of the present invention.

In FIG. 3, a timing diagram is shown describing the operation of the device 10 in one embodiment of the invention. The timing diagram of FIG. 3 extends over three cardiac cycles 120, 140, and 160. In Cardiac cycle 120, an atrial pacing pulse 122 causes an atrial evoked response 124. Then, after a base AV interval 126, a ventricular pacing pulse 128 is issued causing a ventricular evoked response 130. Upon issuance of the ventricular pacing pulse 128, the refractory circuit 73 (FIG. 2) provides a base PVARP 132.

During the cardiac cycle, a timer, such as timing control 79, times out to call for an AV interval extension by hysteresis circuit 71 to encourage intrinsic activity of the heart. Hence, upon the issuance of atrial pacing pulse 142, the AV hysteresis circuit 71 establishes an extended AV interval 144 comprising the base AV interval 126 and an added AV interval extension 146. Also, responsive to the AV interval extension 146 being established by the AV hysteresis circuit 71, the refractory circuit 73 establishes an extended PVARP 150 following the ventricular pacing pulse 148. The extended PVARP 150 comprises the base refractory period 132 plus the refractory period extension 152.

As may be noted in FIG. 3, The AV interval extension has resulted in a retrograde P wave 154. The retrograde P wave might have caused a PMT to develop if it were not for the extended PVARP 150. More specifically, the retrograde P wave 154 has occurred during the extended PVARP 150. Hence while the retrograde P wave is sensed by the sensing circuit 82, it is not responded to for the initiation of an AV interval. Rather, a ventricular pacing pulse 168 is not again issued until it is regularly scheduled to issue.

Because the retrograde P wave 154 is sensed during the extended PVARP, the AV hysteresis circuit 71 responds by restoring the AV interval to the base interval 126 in the next cardiac cycle 160. The refractory circuit 73 then responds to the AV hysteresis circuit 71 restoring the AV interval to the base AV interval by in turn restoring the PVARP to the base PVARP 132 during the next cardiac cycle 160.

Cycle 140 may be repeated for a programmable number of cycles, default being 1, to assure that the P wave 154 detected within the PVARP extension 152 is consistent and related to the ventricular paced event 148 associated with the extended AV delay 144 rather than a coincidental native P wave. If P wave 154 was coincidental, it would not be present on the subsequent cycles.

Figure 4:
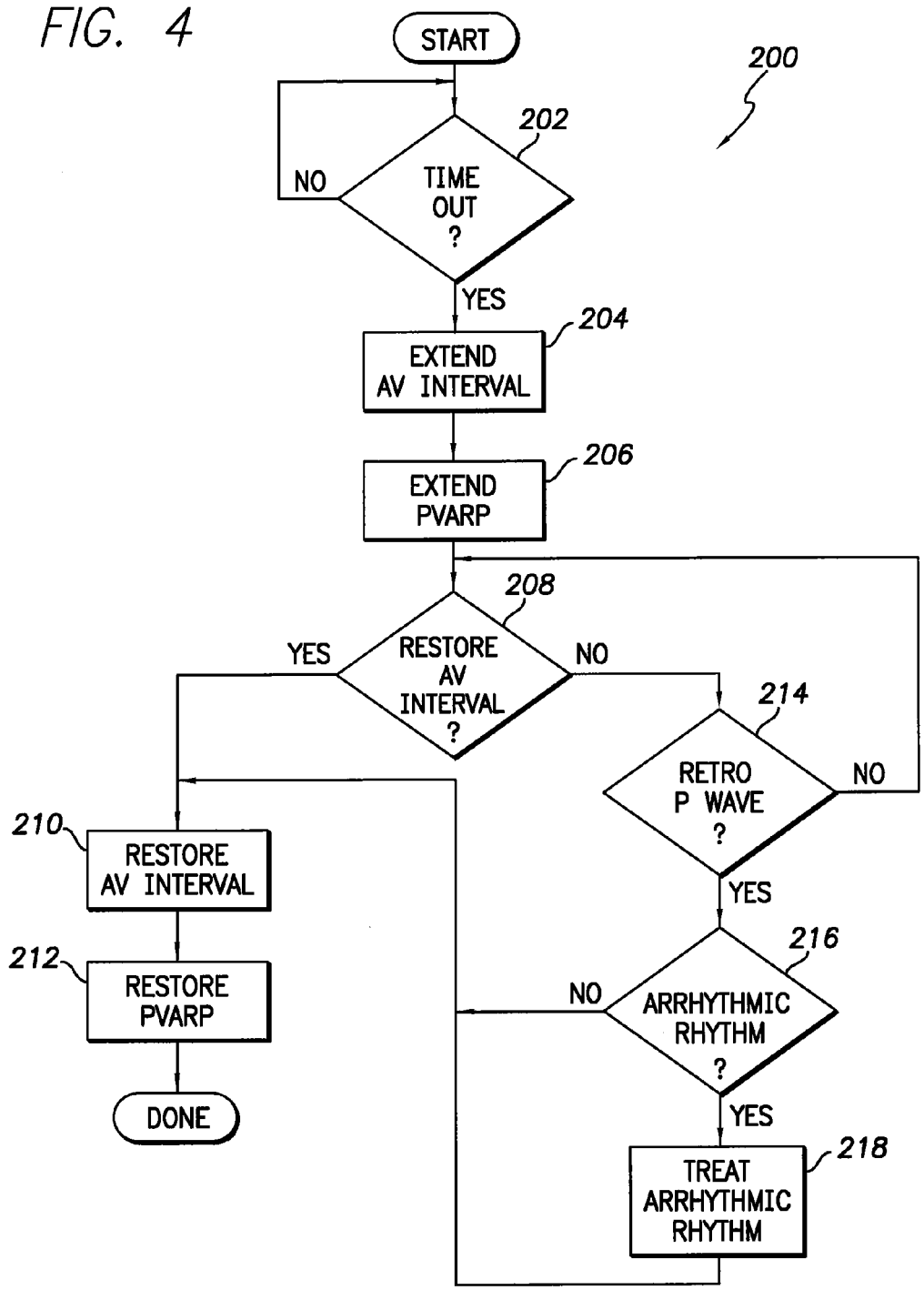
FIG. 4 is a flow chart describing an overview of the operation of one embodiment of the present invention.

In FIG. 4, a flow chart is shown describing an overview of the operation and novel features implemented in one embodiment of the device 10 operating in a mode wherein AV pacing with AV hysteresis is enabled. In this flow chart the various algorithmic steps are summarized in individual "blocks". Such blocks describe specific actions or decisions that must be made or carried out as the algorithm proceeds. Where a microcontroller (or equivalent) is employed, the flow charts presented herein provide the basis for a "control program" that may be used by such a microcontroller (or equivalent) to effectuate the desired control of the stimulation device. Those skilled in the art may readily write such a control program based on the flow charts and other descriptions presented herein.

The process 200 of FIG. 4 initiates with decision block 202. Here it is determined if it is time for the hysteresis circuit 71 to extend the AV interval to encourage intrinsic activity of the heart. If not, the process returns. If it is time to extend the AV interval, the process advances to activity block 204 where the hysteresis circuit 71 extends the AV interval by, for example, adding an AV interval extension to a base AV interval. The process then advances to activity block 206 where, responsive to the hysteresis circuit 71 extending the AV interval, the refractory circuit 73 extends the PVARP. The PVARP may be extended, for example, as previously described, by adding a PVARP extension to a base PVARP. The PVARP extension may have a fixed value and be programmable.

The process 200 then advances to decision block 208. Here it is determined if the conditions exist to restore the AV interval back to the base AV interval. This may be required, for example, if there has been a ventricular pacing pulse issued in the demand mode with the extended AV interval. Different or additional criteria may be imposed on this step without departing from the invention. If restoring the AV interval to the base value is required, the process advances to activity block 210 where the hysteresis circuit 71 restores the AV interval to the base values. Next, in activity block 212, the refractory circuit 73 restores the PVARP to the base PVARP value. The process then returns.

If in decision block 208 restoration of the AV interval to the base value is not yet required, the process advances to decision block 214 to determine if a retrograde P wave has been sensed during the extended PVARP. If not, the process returns to decision block 208. If a retrograde P wave has been sensed, the process advances to decision block 216 to determine if the extended AV interval has resulted in an arrhythmic rhythm, such as an RNRVAS rhythm or AVNRT rhythm. If not, the process advances to activity block 210. If, however, an arrhythmic rhythm has developed, such as an RNRVAS rhythm or AVNRT rhythm, the process advances to activity block 218 where the therapy control causes the appropriate therapy to be administered by the device.

If, for example, the arrhythmic rhythm is an RNRVAS, the therapy control may lengthen the atrial escape interval for at least one cycle as described in the aforementioned U.S. Pat.

No. 6,498,949, incorporated in its entirety herein by reference. If the arrhythmic rhythm is an AVNRT, the extended PVARP may be shortened, e.g., restored to its base value, thus allowing the retrograde P wave to be detected and a ventricular pulse triggered at a shorter PV delay that starts with the P refractory event.

The process then advances to activity block 210 for restoration of the AV interval to the base interval and to activity block 212 for restoration of the PVARP to the base PVARP, if not already done during arrhythmic treatment. The process then returns.

While the invention has been described by means of specific embodiments and applications thereof, it is understood that numerous modifications and variations may be made thereto by those skilled in the art without departing from the spirit and scope of the invention. For example, in that PVARP extension algorithms may be associated with blocking detection of appropriate events but these are likely to occur sporadically rather than consistently with each PVARP extension, if after a programmable number (n) of PVARP extensions, there is no P wave identified in the extended PVARP, then the algorithm may automatically disengage. The clinician can re-engage the algorithm using the programmer at a time of a regularly scheduled follow-up visit. It is therefore to be understood that within the scope of the claims, the invention may be practiced otherwise than as specifically described herein.

What is claimed is:

1. An implantable cardiac stimulation system comprising:
a pulse generator that provides atrial and ventricular pacing stimulation pulses on demand, the pulse generator further providing an AV interval;
an AV hysteresis circuit that extends the AV interval from a base AV interval to an extended AV interval to promote intrinsic heart activity;
a refractory circuit that establishes a PVARP following each provided ventricular pacing pulse including a lengthened PVARP longer in duration than a normal PVARP responsive to the AV hysteresis circuit extending the AV interval from the base AV interval to the extended AV interval; and
a sensing circuit that senses retrograde P waves occurring during an extended PVARP;
wherein the AV hysteresis circuit restores the AV interval to the base AV interval in response to the sensing circuit sensing a retrograde P wave during an extended PVARP and the AV refractory circuit restores the PVARP to the normal PVARP in response to the AV hysteresis circuit restoring the AV interval to the base AV interval.

2. The device of claim 1, wherein the refractory circuit establishes the lengthened PVARP by providing a PVARP extension to a base PVARP.

3. The device of claim 2, wherein the PVARP extension is of fixed duration.

4. The device of claim 3, wherein the PVARP extension is a programmable parameter.

5. An implantable cardiac stimulation system comprising:
a pulse generator that provides atrial and ventricular pacing stimulation pulses on demand, the pulse generator further providing an AV interval;
an AV hysteresis circuit that extends the AV interval from a base AV interval to an extended AV interval to promote intrinsic heart activity; and
a refractory circuit that establishes a PVARP following each provided ventricular pacing pulse including a lengthened PVARP longer in duration than a normal PVARP responsive to the AV hysteresis circuit extending the AV interval from the base AV interval to the extended AV interval;
a sensing circuit that senses retrograde P waves occurring during an extended PVARP; and
an arrhythmia detector that detects for an arrhythmic cardiac rhythm responsive to the sensing circuit sensing a retrograde P wave occurring during an extended PVARP.

6. The device of claim 5, further comprising a therapy control that provides a corrective therapy responsive to the arrhythmia detector detecting an arrhythmic cardiac rhythm.

7. The device of claim 6, wherein the AV hysteresis circuit restores the AV interval to the base AV interval and the refractory circuit restores the PVARP to a base PVARP responsive to the therapy circuit providing the corrective therapy.

8. The device of claim 6, where the arrhythmic cardiac rhythm is a repetitive non-reentrant ventriculo-atrial synchronous (RNRVAS) rhythm.

9. The device of claim 8, wherein the pulse generator further provides an atrial escape interval and wherein the therapy control lengthens the atrial escape interval responsive to the arrhythmia detector detecting an RNRVAS rhythm.

10. In an implantable cardiac stimulation system, a method comprising:
providing atrial and ventricular pacing stimulation pulses on demand with an AV interval;
extending the AV interval from a base AV interval to an extended AV interval to promote intrinsic heart activity;
establishing a PVARP following each provided ventricular pacing pulse;
lengthening the PVARP to a PVARP longer in duration than a normal PVARP responsive to extending the AV interval from the base AV interval to the extended AV interval;
restoring the AV interval to the base AV interval in response to sensing a retrograde P wave during an extended PVARP; and
restoring the PVARP to the normal PVARP in response to the AV interval being restored to the base AV interval.

11. The method of claim 10, wherein lengthening comprises providing a PVARP extension to a base PVARP.

12. The method of claim 10, further comprising sensing retrograde P waves occurring during an extended PVARP.

13. The method of claim 10 further comprising:
repeating the extending, establishing and lengthening for a number of AV cycles; and
sensing for retrograde P waves occurring during extended PVARPs within consecutive AV cycles.

14. In an implantable cardiac stimulation system, a method comprising:
providing atrial and ventricular pacing stimulation pulses on demand with an AV interval;
extending the AV interval from a base AV interval to an extended AV interval to promote intrinsic heart activity;
establishing a PVARP following each provided ventricular pacing pulse;
lengthening the PVARP to a PVARP longer in duration than a normal PVARP responsive to extending the AV interval from the base AV interval to the extended AV interval;
sensing retrograde P waves occurring during an extended PVARP; and
detecting for an arrhythmic cardiac rhythm responsive to sensing a retrograde P wave occurring during an extended PVARP.

15. The method of claim 14, further comprising providing a corrective therapy for the arrhythmic cardiac rhythm responsive to detecting the arrhythmic cardiac rhythm.

16. The method of claim 15, further comprising restoring the AV interval to the base AV interval and restoring the PVARP to a base PVARP responsive to providing the corrective therapy.

17. In an implantable cardiac stimulation system, a method comprising:
  providing atrial and ventricular pacing stimulation pulses on demand with an AV interval;
  extending the AV interval from a base AV interval to an extended AV interval to promote intrinsic heart activity;
  establishing a PVARP following each provided ventricular pacing pulse;
  lengthening the PVARP to a PVARP longer in duration than a normal PVARP responsive to extending the AV interval from the base AV interval to the extended AV interval;
  repeating the extending, establishing and lengthening for a number of AV cycles;
  sensing for retrograde P waves occurring during extended PVARPs within consecutive AV cycles; and
  further comprising at least one of the following:
  restoring the AV interval to the base AV interval in response to sensing a retrograde P wave during consecutive extended PVARPs;
  restoring the PVARP to the normal PVARP in response to sensing a retrograde P wave during consecutive extended PVARPs; and
  detecting for an arrhythmic cardiac rhythm responsive to sensing a retrograde P wave occurring during consecutive extended PVARPs.

* * * * *